United States Patent [19]

Fogarty et al.

[11] Patent Number: 4,611,593

[45] Date of Patent: Sep. 16, 1986

[54] VESSEL OCCLUDING INSTRUMENT

[75] Inventors: Thomas J. Fogarty, 770 Welch Rd., Suite 216, Palo Alto, Calif. 94304; James C. Finn, III, Atherton, Calif.; Thomas B. Kinney, Mountain View, Calif.; George D. Hermann, Palo Alto, Calif.

[73] Assignee: Thomas J. Fogarty, Palo Alto, Calif.

[21] Appl. No.: 677,561

[22] Filed: Dec. 3, 1984

[51] Int. Cl.⁴ .............................................. A61B 17/12
[52] U.S. Cl. ................................... 128/325; 128/327
[58] Field of Search ............... 128/325, 327, 326, 346; 24/481, 571, 16 PB, 483

[56] References Cited

U.S. PATENT DOCUMENTS

| | | | |
|---|---|---|---|
| 3,166,072 | 1/1965 | Sullivan, Jr. | 128/346 |
| 3,880,166 | 4/1975 | Fogarty | 128/325 |
| 3,993,076 | 11/1976 | Fogarty | 128/325 |
| 4,135,749 | 1/1979 | Caveney et al. | 24/16 PB |
| 4,233,980 | 11/1980 | McRae et al. | 128/325 |
| 4,390,019 | 6/1983 | LeVeen et al. | 128/325 |

Primary Examiner—Robert P. Swiatek
Assistant Examiner—Cary E. Stone
Attorney, Agent, or Firm—Limbach, Limbach & Sutton

[57] ABSTRACT

A vessel occluding instrument for facilitating the surgical treatment of an anatomical vessel. The instrument comprises an elongated body member having top and bottom surfaces, opposed sides, and first and second opposed ends; a length of resilient tape extending from adjacent the first opposed end of the body member; a securing device positioned adjacent the second opposed end for releasably holding the resilient tape; and a resilient pad secured to the bottom surface of the body member, the resilient pad comprising a cohesive-adhesive covering sheet for releasing securing the pad to the vessel, whereby the sheet and the vessel collectively produce an adherence relationship therebetween.

7 Claims, 7 Drawing Figures

VESSEL OCCLUDING INSTRUMENT

DESCRIPTION

1. Technical Field

This invention relates to vessel occluding instruments which are used to facilitate the surgical treatment of anatomical vessels.

2. Background Art

Atraumatic means for occluding blood vessels during coronary artery surgery has been used for many years. Atraumatic occluding instruments are used to prevent damage to fragile coronary vessels which may occur if conventional instruments such as clamps or clips are used.

The ideal atraumatic occluding instrument should provide not only occlusive forces on the vessel but also sufficient traction in order to facilitate the surgical procedure. Since vessels come in various dimensions and with different physical conditions, the ideal occluding instrument should be capable of readily adjusting to these variables. For example, the occluding portions of the instrument should be capable of deforming readily to accommodate the irregular shapes of atherosclerotic plaques which are attached to the interior surfaces of vessels in order to reduce the possibility of disrupting these plaques. This deformation capability also permits the occluding instrument to clamp over indwelling catheters which are used for dilation, irrigation, aspiration and infusion of vessels during reconstructive procedures. Moreover, the ideal occluding instrument should be not only easy to apply and remove from vessels but also sufficiently small in size as not to obstruct the operative field.

Although some of these features are disclosed in prior art patents such as U.S. Pat. No. 3,880,166 and U.S. Pat. No. 3,993,076, many are not.

DISCLOSURE OF THE INVENTION

In view of the prior art, it is a major object of the present invention to provide a novel atraumatic occluding instrument that is capable of adhering to the outer surface of the blood vessel in order to improve traction and prevent slipping between the instrument and the vessel.

It is another object of the present invention to provide a novel atraumatic occluding instrument the occluding portion of which comprises an elastomeric cushion and a cohesive-adhesive covering sheet.

It is a further object of the present invention to provide a novel atraumatic occluding instrument the securing means of which is capable of being adjusted readily such that the occlusive and tractive forces on the occluded vessel could be varied easily.

It is another object of the present invention to provide a novel atraumatic occluding instrument where one of the occluding portions is secured to the instrument in a more simplified and effective fashion.

In order to accomplish the above and still further objects, the present invention provides a novel atraumatic vessel occluding instrument for facilitating the surgical treatment of an anatomical vessel. The instrument comprises an elongated body member, a length of resilient tape, securing means and resilient pad means.

More particularly, the elongated body member has top and bottom surfaces, opposed sides, first and second opposed ends.

The length of resilient tape extends from adjacent the first opposed end of the body member. The first opposed end of the body member includes a passageway, extending from the top surface of the body member to the bottom surface, the axis of the passageway being generally perpendicular to the top and bottom surfaces such that a generally vertical passageway is defined. The passageway, adapted to receive the tape, has a horizontal cross-sectional dimension that is smaller than the horizontal cross-sectional dimension of the tape, whereby the tape is securely retained in the passageway.

The securing means, positioned at the second opposed end for releasably holding the resilient tape, includes an upwardly extending latching means which is adapted for releasably securing the tape.

The resilient pad means, secured to the bottom surface of the body member, comprises a cohesive-adhesive covering sheet for releasably securing the pad means to the vessel, whereby the covering sheet and the vessel collectively produce an adherence relationship therebetween. In the preferred embodiment, the resilient pad means further comprises an elastomeric cushion. The elastomic cushion is positioned between the cohesive-adhesive covering sheet and the bottom surface of the body member.

The occluding instrument in the preferred embodiment further comprises an instrument positioning means. The positioning means is an upwardly-extending protrusion of the top surface of the body member.

One advantage of the present invention is that the occluding instrument, utilizing the cohesive-adhesive feature of the covering sheet of its resilient pad means, is capable of adhering to the outer, adventitial layer of the blood vessel. Such adherence provides improved traction between the instrument and the vessel such that slipping between the instrument and the vessel during surgery is prevented.

Another advantage of the present invention is that the resilient pad means comprises the elastomeric cushion and the cohesive-adhesive covering sheet.

A further advantage of the present invention is that the latching means of the securing means is capable of being readily adjusted such that the occlusive and tractive forces on the occluded vessel may be easily varied.

Another advantage of the present invention is that the resilient tape, one of the occluding portions of the instrument, is secured to the instrument in a simplified and effective fashion.

It is a still further advantage of the present invention that the instrument positioning means permits the easy positioning and maneuvering of the instrument.

Other objects, features, and advantages of the present invention will appear from the following detailed description of the best mode of a preferred embodiment, taken together with the accompanying drawing.

BEST MODE FOR CARRYING OUT THE INVENTION

Figure 2:
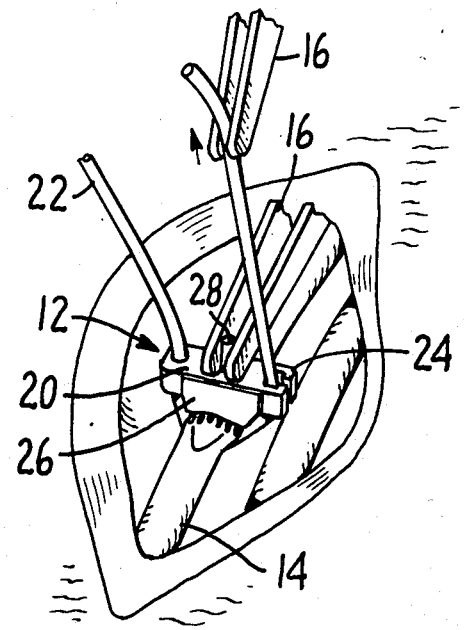
FIG. 2 is a perspective view of the occluding instrument of FIG. 1 when it is attached to a vessel, a portion of which is being occluded by the instrument.
Figure 1:
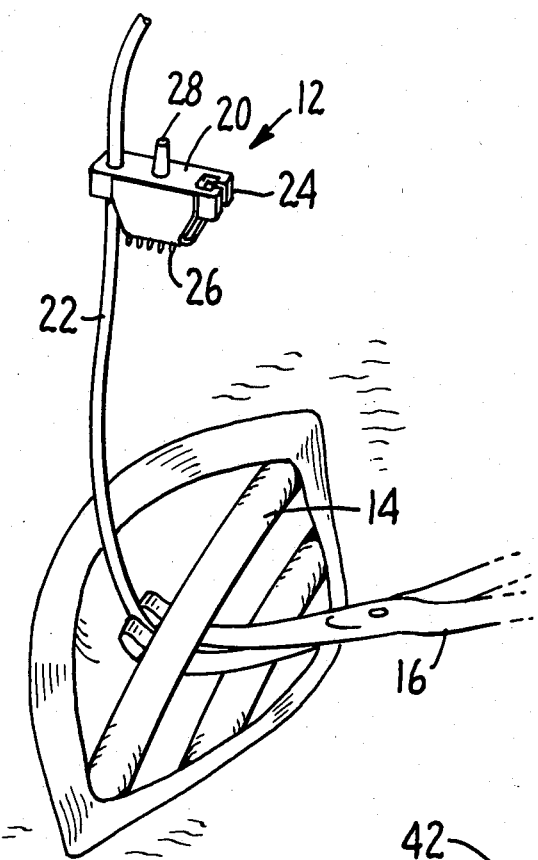
FIG. 1 is a perspective view of the novel atraumatic vessel occluding instrument of the present invention as it is being attached to a blood vessel.

Referring to FIG. 1, there is shown a vessel occluding instrument, generally designated 12, as it is being attached to a coronary blood vessel 14. An instrument such as a forcep 16 is generally used in assisting the attachment of instrument 12 to vessel 14. FIG. 2 generally shows instrument 12, fully attached to vessel 14, as it occludes a segment of vessel 14.

Vessel occluding instrument 12 comprises an elongated body member 20, a length of resilient tape 22, securing means 24, resilient pad means 26, and instrument positioning means 28.

Figure 3:
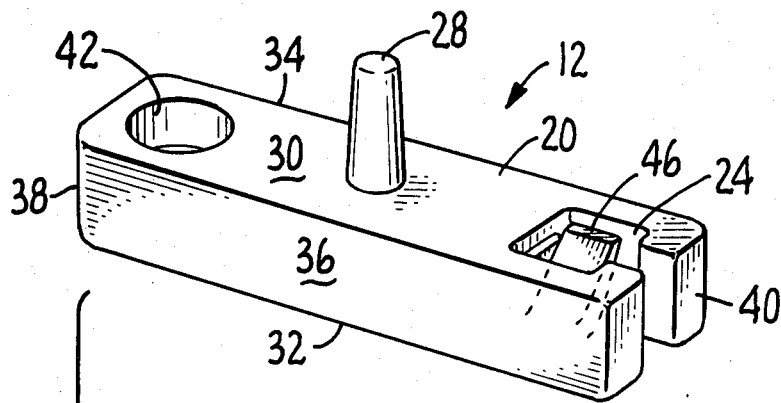
FIG. 3 is an exploded perspective view of the occluding instrument of FIGS. 1 and 2, without the resilient tape.
Figure 3:
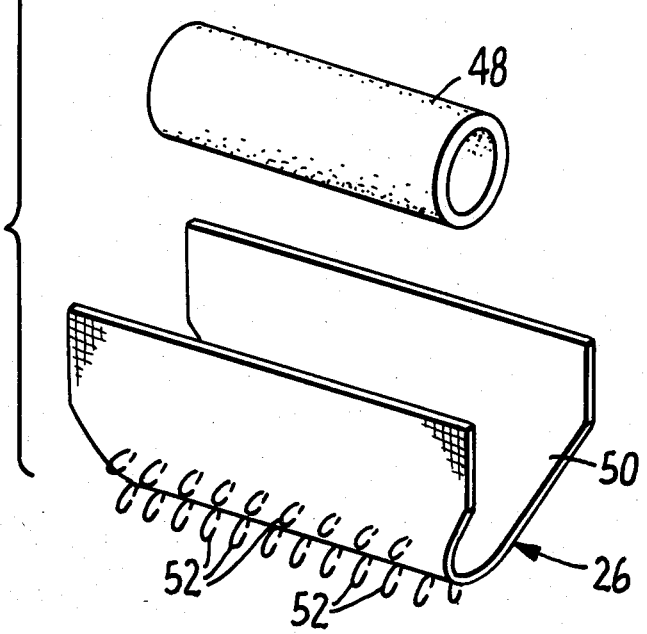
Figure 4:
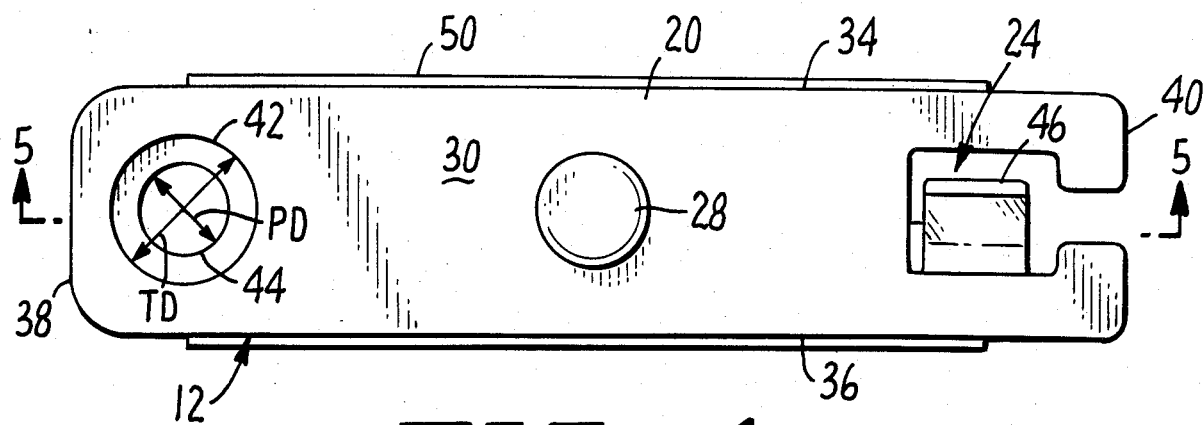
FIG. 4 is a top view of the occluding instrument of FIG. 3.

More particularly, as best shown in FIGS. 3 and 4, elongated body member 20 has top surface 30, bottom surface 32, opposed sides 34, 36, first opposed end 38, and second opposed end 40.

Figure 5:
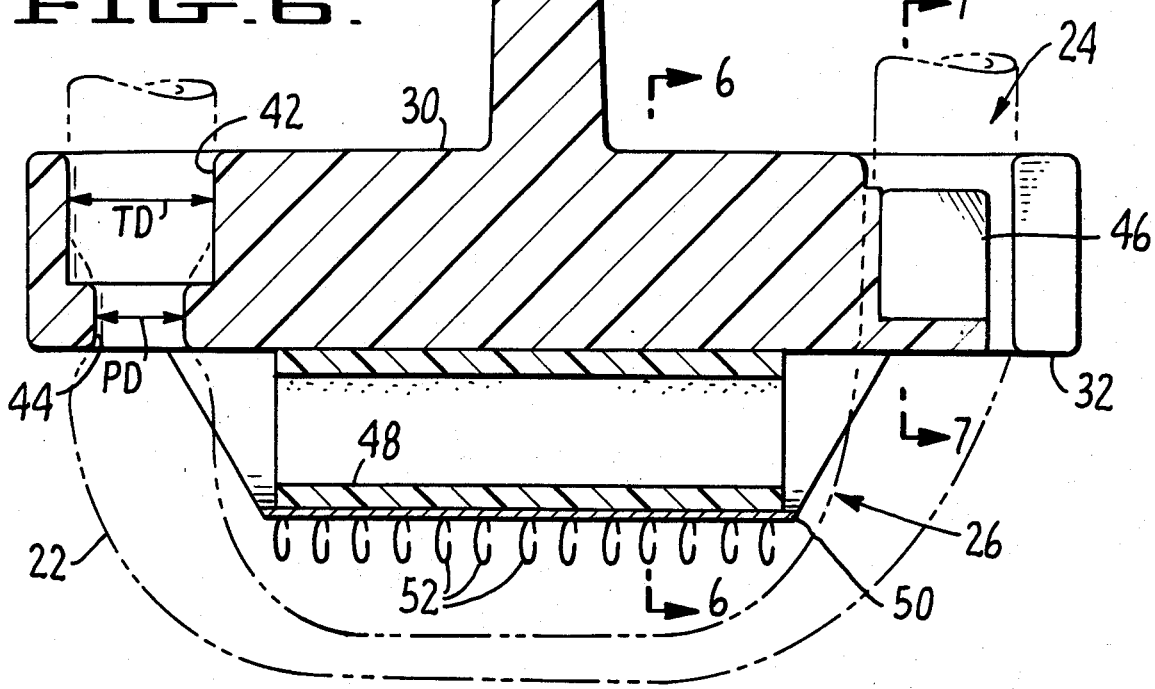
FIG. 5 is a cross section view of the occluding instrument of FIG. 4, taken along line 5—5, with the resilient tape in phantom.

As best shown in FIGS. 1 and 2, resilient tape 22 extends from adjacent first opposed end 38. Tape 22 is generally an elastomeric tube which is made from conventional white silicone rubber. As best shown in FIGS. 4 and 5, first opposed end 38 includes a passageway 42. Passageway 42 extends from top surface 30 of body member 20 to bottom surface 32. Since the axis of passageway 42 is generally perpendicular to top and bottom surfaces 30, 32, passageway 42 is a generally vertical passageway. Passageway 42, which is adapted to receive tape 22, has a horizontal cross-sectional dimension that is smaller than the horizontal cross-sectional dimension of tape 22. In the preferred embodiment, as best shown in FIGS. 4 and 5, passageway 42 has an inner cylindrical passageway 44 the diameter PD of which is smaller than the diameter TD of tape 22, shown as dotted line in FIG. 5. Since diameter PD of passageway 42 is smaller than diameter TD of tape 22, tape 22 is securely retained in passageway 42, thereby eliminating other securing features such as knots, loops, diagonal passageways, etc. of prior art instruments.

Next, securing means 24, positioned adjacent second opposed end 40, is provided to releasably hold resilient tape 22 when instrument 12 is occluding vessel 14, as best shown in FIG. 2. As best shown in FIGS. 3, 4, 5 and 7, securing means 24 includes an upwardly extending latch 46. Latch 46, positioned at an angle oblique to the axis of tape 22, is adapted to hold securely tape 22 in securing means 24.

Figure 6:
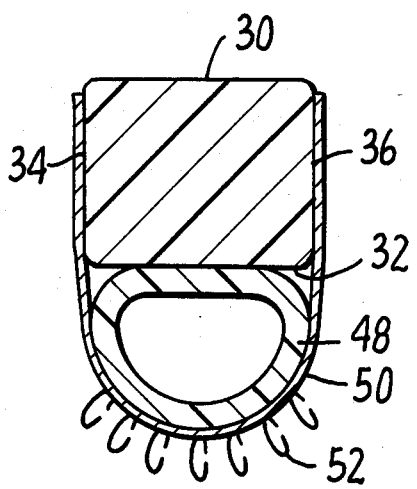
FIG. 6 is a side cross section view of the occluding instrument of FIG. 5, taken along line 6—6.
Figure 7:
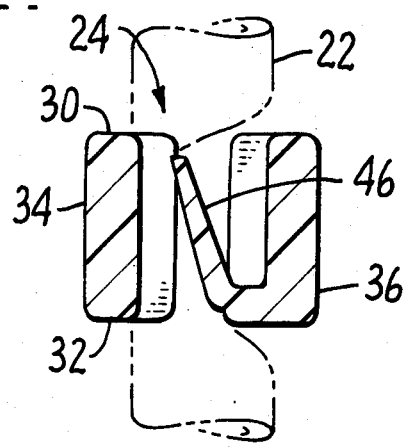
FIG. 7 is side cross section view of the occluding instrument of FIG. 5, taken along line 7—7.

Further, resilient pad means 26, as best shown in FIGS. 3, 5 and 6, is secured to bottom surface 32 of body member 20. Resilient pad means 26 comprises an elastomeric cushion 48 and a cohesive-adhesive covering sheet 50, as best shown in FIG. 3. Elastomeric cushion 48, in the preferred embodiment is a length of resilient surgical tubing similar to tape 22. Covering sheet 50, covering cushion 48, has Velcro-like loops 52 on it. Such loops 52 are capable of interacting with the external adventitial layer of blood vessel 14 to create an adherence relationship similar to the bonding effect of Velcro materials—the loops attaching to the felt-like Velcro material. The adherence relationship improves the traction between instrument 12 and vessel 14 by preventing slipping between the two.

Moreover, as best shown in FIGS. 3 and 5, instrument positioning means 28 is an upwardly-extending protrusion of top surface 30 of body member 20.

In use, one end of surgical tape 22 is brought around coronary vessel 14. Surgical instruments such as forceps 16 may be used. Similarly, forcep 16, grasping positioning means 28, may be used to position occluding instrument 12. Velcro-like loops 52 are then capable of attaching to the external adventitial tissue of vessel 14 to facilitate the subsequent occlusion phase of the operation. With forcep 16 and Velcro-like loops 52 holding instrument 12 in the desired position, as best shown in FIG. 2, resilient tape 22 is then pulled through securing means 24 until blood ceases to flow through vessel 14. The position of tape 22 is secured by latch 46. Vessel 14 is now resting between two resilient, atraumatic surfaces—tape 22 and Velcro-covered elastomeric cushion 48.

While vessel 14 is being occluded, Velcro covering sheet 50, attached to the adventitial tissue of vessel 14, also prevents slippage between instrument 12 and vessel 14. In addition, the occlusive and tractive forces on vessel 14 may be easily and quickly adjusted by removing tape 22 from latch 46.

It will be apparent to those skilled in the art that various modifications may be made within the spirit of the invention and the scope of the appended claims.

We claim:

1. A vessel occluding instrument for facilitating the surgical treatment of an anatomical vessel, said instrument comprising an elongated body member having top and bottom surfaces, opposed sides, and first and second opposed ends;

a length of resilient tape extending from adjacent said first opposed end of said body member;

securing means positioned adjacent said second opposed end for releasably holding said resilient tape; and resilient pad means secured to said bottom surface of said body member, said resilient pad means comprising a cohesive-adhesive covering sheet for releasably and atraumatically securing said pad means to said vessel, whereby said sheet and said vessel collectively produce an adherence relationship therebetween.

2. The vessel occluding instrument as claimed in claim 1, wherein said resilient pad means further comprises an elastomeric cushion, said elastomeric cushion being positioned between said cohesive-adhesive covering sheet and said bottom surface of said body member.

3. A vessel occluding instrument for facilitating the surgical treatment of an anatomical vessel, said instrument comprising an elongated body member having top and bottom surfaces, opposed sides, and first and second opposed ends;

a length of resilient tape extending from adjacent said first opposed end of said body member;

securing means positioned adjacent said second opposed end for releasably holding said resilient tape, said securing means includes an upwardly-extending latching means which is adapted for releasably securing said tape; and resilient pad means secured to said bottom surface of said body member, said resilient pad means comprising a cohesive-adhesive covering sheet for releasably and atraumatically securing said pad means to said vessel, whereby said sheet and said vessel collectively produce an adherence relationship therebetween.

4. A vessel occluding instrument for facilitating the surgical treatment of an anatomical vessel, said instrument comprising an elongated body member having top and bottom surfaces, opposed sides, and first and second opposed ends;

a length of resilient tape extending from adjacent said first opposed end of said body member, said first opposed end of said body member includes a passageway, extending from said top surface of said body member to said bottom surface, the axis of said passageway being generally perpendicular to said top and bottom surfaces defining a generally vertical passageway;

said passageway, adapted to receive said tape, has a horizontal cross-sectional dimension that is smaller than the hrizontal cross-sectional dimension of said tape, whereby said tape is securely retained in said passageway;

securing means positioned adjacent said second opposed end for releasably holding said resilient tape; and resilient pad means secured tosaid bottom surface of said body member, said resilient pad means comprising a cohesive-adhesive covering sheet for releasably and atraumatically securing said pad means to said vessel, whereby said sheet and said vessel collectively produce an adherence relationship therebetween.

5. A vessel occluding instrument for facilitating the surgical treatment of an anatomical vessel, said instrument comprising an elongated body member having top and bottom surfaces, opposed sides, and first and second opposed ends;

a length of resilient tape extending from adjacent said first opposed end of said body member, said first opposed end of said body member includes a passageway, extending from said top surface of said body member to said bottom surface, the axis of said passageway being generally perpendicular to said top and bottom surfaces defining a generally vertical passageway;

said passageway, adapted to receive said tape, has a horizontal cross-sectional dimension that is smaller than the horizontal cross-sectional dimension of said tape, whereby said tape is securely retained in said passageway;

securing means positioned adjacent said second opposed end for releasably holding said resilient tape, said securing means includes an upwardly extending latching means which is adapted for releasably securing said tape; and resilient pad means secured to said bottom surface of said body member, said resilient pad means comprising a cohesive-adhesive covering sheet for releasably and atraumatically securing said pad means to said vessel, whereby said covering sheet and said vessel collectively produce an adherence relationship therebetween.

6. The vessel occluding instrument as claimed in claim 5, wherein said resilient pad means further comprises an elastomeric cushion, said elastomic cushion being positioned between said cohesive-adhesive covering sheet and said bottom surface of said body member.

7. The vessel occluding instrument as claimed in claim 5 or 6, further comprising an instrument positioning means, said positioning means being an upwardly-extending protrusion of said top surface of said body member.

* * * * *

UNITED STATES PATENT AND TRADEMARK OFFICE

CERTIFICATE

Patent No. 4,611,593                   Patented: September 16, 1986

On petition requesting issuance of a certificate for correction
of inventorship pursuant to 35 USC 256, it has been found that
the above-identified patent, through error and without any
deceptive intent, improperly sets forth the inventorship.
Accordingly, it is hereby certified that the correct inventorship
of this patent is Thomas J. Fogarty.

Signed and Sealed this Thirteenth Day of December, 1988.

Abraham Hershkovitz
Petitions Examiner
Office of the Deputy Assistant
  Commissioner for Patents